(12) United States Patent
Foley et al.

(10) Patent No.: US 11,919,849 B2
(45) Date of Patent: Mar. 5, 2024

(54) METHODS FOR HYDRODEALKENYLATION

(71) Applicant: P2 SCIENCE, INC., Woodbridge, CT (US)

(72) Inventors: Patrick Foley, New Haven, CT (US); Ashoke Bhattacharjee, Cheshire, CT (US); Yonghua Yang, Niantic, CT (US); Yong J. Tu, Cheshire, CT (US)

(73) Assignee: P2 SCIENCE, INC, Woodbridge, CT (US)

( * ) Notice: Subject to any disclaimer, the term of this patent is extended or adjusted under 35 U.S.C. 154(b) by 0 days.

(21) Appl. No.: 17/772,373

(22) PCT Filed: Jun. 17, 2021

(86) PCT No.: PCT/US2021/037964
§ 371 (c)(1),
(2) Date: Apr. 27, 2022

(87) PCT Pub. No.: WO2021/257922
PCT Pub. Date: Dec. 23, 2021

(65) Prior Publication Data
US 2023/0046311 A1  Feb. 16, 2023

Related U.S. Application Data

(60) Provisional application No. 63/041,411, filed on Jun. 19, 2020.

(51) Int. Cl.
*C07C 67/08* (2006.01)
*C07C 29/00* (2006.01)

(52) U.S. Cl.
CPC .............. *C07C 67/08* (2013.01); *C07C 29/00* (2013.01)

(58) Field of Classification Search
CPC ....... C07C 67/08; C07C 29/00; C07C 315/02; C07C 319/14
See application file for complete search history.

(56) References Cited

U.S. PATENT DOCUMENTS

| | | | | |
|---|---|---|---|---|
| 3,296,318 A * | 1/1967 | Starks | ................... | C07C 29/84 568/918 |
| 3,666,726 A * | 5/1972 | Grogler | ................ | C08G 18/675 528/26 |
| 4,000,340 A * | 12/1976 | Murphy | ................ | C11D 3/2013 428/34.3 |
| 4,006,109 A * | 2/1977 | Ochsner | ................ | C07D 315/00 568/903 |
| 6,022,531 A * | 2/2000 | Giersch | .................. | A23L 27/29 424/48 |
| 6,790,463 B2 * | 9/2004 | Hofmann | .................. | A61P 9/10 424/722 |
| 6,794,356 B2 * | 9/2004 | Turner | ..................... | C11D 3/48 510/516 |
| 2009/0232761 A1 * | 9/2009 | Faergemann | ........... | A61L 9/145 424/76.8 |

FOREIGN PATENT DOCUMENTS

| | | | | |
|---|---|---|---|---|
| EP | 1068862 A2 * | 1/2001 | ............... | A61K 8/34 |
| EP | 3470388 A1 * | 4/2019 | ............ | C07C 29/44 |
| JP | S50088234 | * 7/1975 | | |
| WO | WO-2017214446 A1 * | 12/2017 | ............... | A23L 2/56 |
| WO | WO-2018171871 A1 * | 9/2018 | ........... | A23L 27/203 |
| WO | WO-2020084477 A1 * | 4/2020 | ............... | A61K 8/22 |
| WO | WO 2020/176386 A2 | 9/2020 | | |

OTHER PUBLICATIONS

Kobayashi, K. et al., Reaction of monoterpene oxides with methanol in the presence of montmorillonite K10 catalyst, Sch. Sci. Technol., Meiji Univ., Kawasaki, Japan, Yukagaku, 43(5) , pp. 416-420, (1 page abstract) (Year: 1994).*
Polster, J. et al., Structure-odor correlations in homologous series of alkanethiols and attempts to predict odor thresholds by 3D-QSAR studies, J. Agricultural and Food Chemistry, 63, pp. 1419-1432 (Year: 2015).*
Smaligo, A., J., et al., Hydrodealkenylative C(sp3)-C(sp2) bond fragmentation, Science, 364(6441), pp. 681-685. (5 pages) (Year: 2019).*
PubChem CID 12242, 2-methyl-2-heptanol, (1 page abstract) (Year: 2005).*
PubChem CID 53425858, (3-methylcyclohexyl)acetate, (1 page abstract) (Year: 2011).*
Jps50088234, Muto et al., Cyclohexyl carboxylates for control of cockroaches, English abstract (1 page) (Year: 1975).*
Fargher, R. G., et al., The action of alpha gamma-dibromobutane on sodium derivatives of ethyl acetoacetate and benzoylacetate, Journal of the Chemical Society, Transactions, 105, pp. 1353-1367 (Year: 1914).*
EP1068862, Diehl et al., Deodorizing active substance combination, English translation, 9 pages (Year: 2001).*
PubChem CID 22311, 59 pages, (2004); retrieved on Apr. 25, 2022 from http://https://pubchem.ncbi.nlm.nih.gov/compound/Limonene.
Sipila et al. "Reactivity of Stabilized Criegee Intermediates (sCIs) from Isoprene and Monoterpene Ozonolysis Toward SO$_2$ and Organic Acids," *Atmos. Chem. Phys.*, vol. 14, pp. 12143-12153, (2014).
Smaligo et al., "Hydrodealkenylative C(sp$^3$)-C(sp$^2$) bond fragmentation," *Science*, vol. 364, pp. 681-685, (2019).

* cited by examiner

*Primary Examiner* — Yate' K Cutliff
(74) *Attorney, Agent, or Firm* — Hoxie & Associates LLC

(57) ABSTRACT

The present disclosure pertains to new methods of performing a hydrodealkenylation of monounsaturated alcohols, thiols, and derivatives thereof, such as terpenes and derivatives, comprising ozonolysis and quenching using a sulfinic acid or sulfinic acid salt.

19 Claims, No Drawings

METHODS FOR HYDRODEALKENYLATION

CROSS-REFERENCE TO RELATED APPLICATIONS

This application is a national stage entry filed under 35 U.S.C. § 371 of international application No. PCT/US2021/037964, filed on Jun. 17, 2021, which claims priority to, and the benefit of, U.S. Provisional Application Ser. No. 63/041,411, filed on Jun. 19, 2020, the contents of each of which are hereby incorporated by reference in their entireties.

FIELD OF INVENTION

The present disclosure pertains to new methods of performing a hydrodealkenylation of monounsaturated alcohols, thiols, and derivatives thereof, such as terpenes and derivatives, comprising ozonolysis and quenching using a sulfinic acid or sulfinic acid salt.

BACKGROUND

Ozonolysis is an industrially useful transformation that involves the oxidation of an unsaturated carbon-carbon bond of an alkene using ozone. The reported mechanism (the "Criegee mechanism") begins with initial formation of a primary ozonide (1,2,3-trioxolane) intermediate which rapidly decomposes into a carbonyl compound and carbonyl oxide compound. This pair of initial intermediates recombine to form a more stable secondary ozonide (1,2,4-trioxolane), a structure featuring a peroxide bridge.

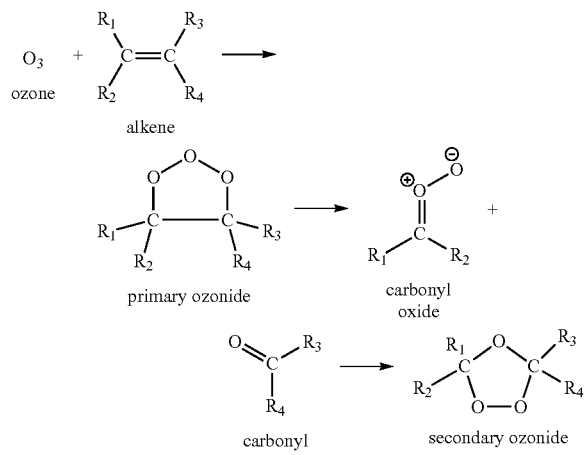

Although more stable than a primary ozonide or a carbonyl oxide, the secondary ozonide is still a high-energy chemical species subject to auto-accelerating thermal decomposition, decomposition to undesirable by-products, and organic peroxide formation (bis-peroxide, poly-peroxide, and hydroperoxide species). Therefore, further reactions must be carefully controlled in order to produce a desired carbonyl product in good yield.

Uncontrolled thermal decomposition of secondary ozonides typically yields highly variable mixtures of products due to the strong driving force of peroxide bond decomposition (highly exothermic) and unselective kinetic pathways such as radical propagation. For these reasons, the secondary ozonide is an undesirable chemical product and must be reacted in a subsequent chemical step.

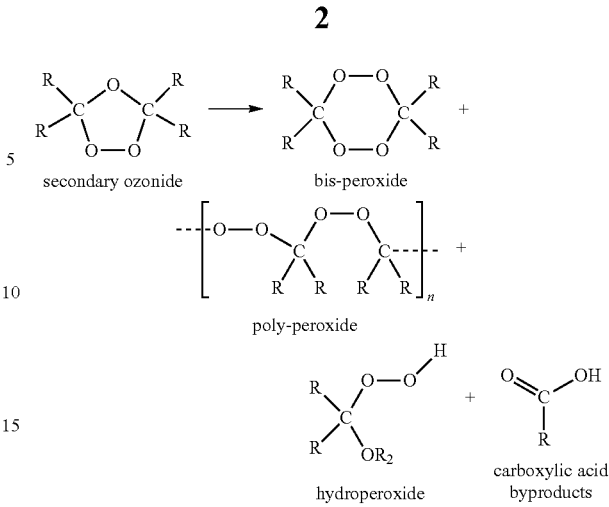

Traditionally, the secondary ozonide intermediates are either oxidatively or reductively cleaved to yield carbonyl products. Oxidative cleavage yields carboxylic acid and/or ketone products. Reductive cleavage yields ketone and/or aldehyde products, which may be further reduced to primary and secondary alcohol products. Thus, under normal conditions, each product of the reaction retains one of the original double bond carbons, but in a higher oxidation state (e.g., a carbonyl or carboxylic acid carbon oxidation state).

Traditional ozonide quenching conditions do not normally result in elimination of both carbon atoms of the original double bond. Smaligo et al. report a radical ozonide cleavage reaction which results in dehydroalkenylation of isopropenylcyclohexanes, but this reaction requires an iron salt reducing agent (e.g., iron sulfate) and the highly malodorous hydrogen donor benzenethiol. *Science* 364: 681-85 (2019).

Vinyl (ethenyl) and isopropenyl side groups are common in natural products, such as terpenes. Many such natural compounds, especially those also containing such functional groups as secondary alcohols, aldehydes, ketones, formates, acetates, and larger esters have desirable organoleptic properties, such as taste and aroma. However, many such compounds, or their precursors, also include undesirable double bonds, short unsaturated side chains, which are prone to decomposition, polymerization and microbial spoilage. An efficient means to remove such unsaturated side chains could provide a highly cost-effective route to such organoleptic compounds using naturally derived (i.e., renewable) starting materials. Such organoleptic compounds can thus find use in a variety of consumer products, including flavors and fragrances, personal care, home care, air care products and the like.

BRIEF SUMMARY OF THE INVENTION

The present disclosure provides a method of making a compound according to Formula 1:

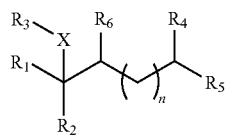

wherein n is an integer from 0-5; X is O or S; $R^3$ is selected from H, $C_{1-6}$alkyl (e.g., methyl), formyl (—CHO), and $C_{2-10}$acyl (e.g., acetyl, propionyl, butyryl, pentanoyl); and each of $R^1$, $R^2$, $R^4$, $R^5$, and $R^6$ are independently selected from H and $C_{1-10}$alkyl, optionally wherein each of said $C_{1-10}$alkyl is further substituted by a group selected from $C_{1-6}$alkyl, hydroxy, $C_{1-6}$alkoxy, formyl, and $C_{2-10}$acyl, or wherein $R^1$ and $R^2$, and/or $R^4$ and $R^5$, and/or $R^2$ and $R^5$, can be taken together to form a $C_{3-8}$carbocyclic ring, wherein such ring is optionally substituted by a group selected from $C_{1-6}$alkyl, hydroxy, $C_{1-6}$alkoxy, formyl, and $C_{2-10}$acyl;

wherein the method comprises the steps of (a) treating the compound of Formula 2,

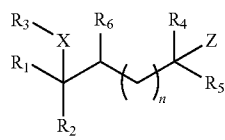

wherein n, X, and each of $R^1$, $R^2$, $R^3$, $R^4$, $R^5$, and $R^6$ are as defined for Formula 1, and wherein Z is selected from vinyl (—CH=CH$_2$) and isopropenyl (—C(CH$_3$)=CH$_2$); with ozone to form an ozonide mixture, and (b) quenching the ozonide mixture with an alpha-hydroxysulfinic acid or alpha-hydroxysulfinic acid salt to yield the compound of Formula 1.

DETAILED DESCRIPTION OF THE INVENTION

It was unexpectedly discovered during a course of research that vinyl and isopropenyl compounds could be dehydroalkenylated by treatment with ozone in a suitable solvent to form an ozonide intermediate mixture, followed by quenching of the ozonide mixture with a reagent system comprising an alpha-hydroxysulfinic acid or alpha-hydroxysulfinic acid, such as sodium hydroxymethanesulfinate. The reaction sequence may be summarized as follows

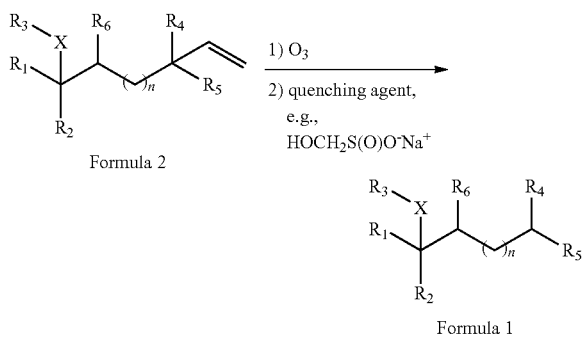

Although the precise mechanism of the reaction has not yet been elucidated, without being bound by theory, it is believed that the reaction involves a radical-mediated one-electron reduction of intermediate ozonide compounds.

In a first aspect, the present disclosure therefore provides, a method (Method 1) of making a compound according to Formula 1:

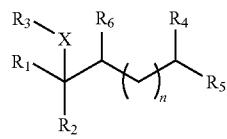

wherein n is an integer from 0-5; X is O or S; $R^3$ is selected from H, $C_{1-6}$alkyl (e.g., methyl), formyl (—CHO), and $C_{2-10}$acyl (e.g., acetyl, propionyl, butyryl, pentanoyl); and each of $R^1$, $R^2$, $R^4$, $R^5$, and $R^6$ are independently selected from H and $C_{1-10}$alkyl, optionally wherein each of said $C_{1-10}$alkyl is further substituted by a group selected from $C_{1-6}$alkyl, hydroxy, $C_{1-6}$alkoxy, formyl, and $C_{2-10}$acyl, or wherein $R^1$ and $R^2$, and/or $R^4$ and $R^5$, and/or $R^2$ and $R^5$, can be taken together to form a $C_{3-8}$carbocyclic ring, wherein such ring is optionally substituted by a group selected from $C_{1-6}$alkyl, hydroxy, $C_{1-6}$alkoxy, formyl, and $C_{2-10}$acyl;

wherein the method comprises the steps of (a) treating the compound of Formula 2,

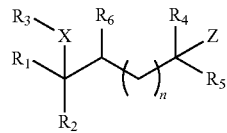

wherein n, X, and each of $R^1$, $R^2$, $R^3$, $R^4$, $R^5$, and $R^6$ are as defined for Formula 1, and wherein Z is selected from vinyl (—CH=CH$_2$) and isopropenyl (—C(CH$_3$)=CH$_2$);

with ozone to form an ozonide mixture, and (b) quenching the ozonide mixture with an alpha-hydroxysulfinic acid or alpha-hydroxysulfinic acid salt quenching agent to yield the compound of Formula 1.

In further embodiments of the first aspect, the present disclosure provides:
1.1 Method 1, wherein the quenching agent is an alpha-hydroxysulfinic acid or alpha-hydroxysulfinic acid salt according to the formula:

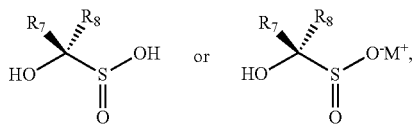

wherein $R^7$ and $R^8$ are each independently selected from $C_{1-6}$alkyl (e.g., methyl), aryl (e.g., phenyl), and heteroaryl (e.g., pyridyl), and wherein M is a metal or ammonium counterion;
1.2 Method 1.1, wherein M is selected from an alkali metal cation (e.g., Li, Na or K), an alkaline earth metal cation (e.g., Ca or Mg), or other monovalent, bivalent or trivalent transition metal or metalloid cation (e.g., Al, Zn, Cu, Sr, Sn, Fe, etc.), or an ammonium ion (NH$^{4+}$ or a tetraalkylammonium ion);
1.3 Method 1.2, wherein M is an alkali metal cation, e.g., Li, Na or K;
1.4 Method 1.1, 1.2, or 1.3, wherein $R^7$ and $R^8$ are each independently H or methyl;

1.5 Method 1.4, wherein $R^7$ and $R^8$ are each independently H;
1.6 Method 1.5, wherein the quenching agent is $HOCH_2S(O)OH$ or $HOCH_2S(O)OM$ wherein M is selected from Li, Na and K;
1.7 Method 1.6, wherein the quenching agent is $HOCH_2(O)ONa$.
1.8 Method 1, or any of 1.1-1.7, wherein X is S;
1.9 Method 1, or any of 1.1-1.7, wherein X is O;
1.10 Method 1, or any of 1.1-1.9, wherein Z is vinyl;
1.11 Method 1, or any of 1.1-1.9, wherein Z is isopropenyl;
1.12 Method 1, or any of 1.1-1.11, wherein $R^3$ is selected from H, methyl, formyl, acetyl, propionyl, butyryl, and pentanoyl;
1.13 Method 1.12, wherein $R^3$ is selected from H and methyl;
1.14 Method 1, or any of 1.1-1.13, wherein n is selected from 0, 1, 2, 3 and 4;
1.15 Method 1, or any of 1.1-1.14, wherein each of $R^1$, $R^2$, $R^4$, $R^5$, and $R^6$ are independently selected from H and $C_{1-6}$alkyl, optionally wherein each of said $C_{1-6}$alkyl is further substituted by $C_{1-4}$alkyl, hydroxy, $C_{1-3}$alkoxy, formyl, or $C_{2-6}$acyl;
1.16 Method 1.15, wherein each of $R^1$, $R^2$, $R^4$, $R^5$, and $R^6$ are independently selected from H, methyl, ethyl, isopropyl, propyl, butyl, s-butyl, isobutyl, t-butyl, and pentyl, and wherein each of said methyl, ethyl, propyl, butyl and pentyl is optionally substituted with methyl, ethyl, isopropyl, t-butyl, hydroxy, methoxy, ethoxy, acetyl or propionyl;
1.17 Method 1.16, wherein each of $R^1$, $R^2$, $R^4$, $R^5$, and $R^6$ are independently selected from H and unsubstituted $C_{1-6}$alkyl;
1.18 Method 1, or any of 1.1-1.17, wherein $R^1$ and $R^2$ and/or $R^4$ and $R^5$ are taken together to form a $C_{3-8}$carbocyclic ring, wherein such ring is optionally substituted by $C_{1-6}$alkyl, hydroxy, $C_{1-6}$alkoxy, formyl, or $C_{2-10}$acyl;
1.19 Method 1.18 wherein said carbocyclic ring is a cyclopentane or cyclohexane ring;
1.20 Method 1.18 or 1.19, wherein said carbocyclic ring is optionally substituted with methyl, ethyl, isopropyl, t-butyl, hydroxy, methoxy, ethoxy, acetyl, and propionyl;
1.21 Method 1, or any of 1.1-1.17, wherein $R^2$ and $R^5$ are taken together to form a $C_{3-8}$ carbocyclic ring, wherein such ring is optionally substituted by $C_{1-6}$alkyl, hydroxy, $C_{1-6}$alkoxy, formyl, or $C_{2-10}$acyl;
1.22 Method 1.21 wherein said carbocyclic ring is a cyclopentane or cyclohexane ring;
1.23 Method 1.21 or 1.22, wherein said carbocyclic ring is optionally substituted with methyl, ethyl, isopropyl, t-butyl, hydroxy, methoxy, ethoxy, acetyl or propionyl;
1.24 Method 1, or any of Methods 1.1-1.23, wherein $R^3$ is selected from H, methyl, formyl and acetyl; $R^1$ and $R^2$ are independently selected from methyl and ethyl; $R^4$ and $R^5$ are independently selected from H, methyl, ethyl and isopropyl; $R^6$ is selected from H and methyl; and n is 1, 2, 3 or 4;
1.25 Method 1, or any of Methods 1.1-1.23, wherein $R^3$ is selected from H, methyl, formyl, acetyl, and propionyl; $R^1$ is methyl or ethyl; $R^4$ and $R^6$ are independently selected from H and methyl; n is 2; and $R^2$ and $R^5$ together with the carbon atoms between them form a cyclohexane ring (i.e., $R^2$ and $R^5$ together form a methylene, —$CH_2$—);
1.26 Method 1, or any of Methods 1.1-1.23, wherein $R^3$ is selected from H, methyl, formyl, and acetyl; $R^1$ is H or methyl; $R^4$ is H or methyl; $R^6$ is methyl or ethyl; n is 2; and $R^2$ and $R^5$ together with the carbon atoms between them form a methyl cyclohexane ring (i.e., $R^2$ and $R^5$ together form a methyl methylene, —CH($CH_3$)—);
1.27 Method 1, or any of Methods 1.1-1.23, wherein $R^3$ is selected from H, methyl, formyl, and acetyl; $R^1$ is methyl or ethyl; $R^2$ is H or methyl; $R^4$ and $R^5$ are each independently H or methyl; and $R^6$ is H or methyl;
1.28 Method 1, or any of Methods 1.1-1.27, wherein the compound of Formula 1 has a mashed-potato, fried, oily, lemon-like, grassy-herbaceous, green-fatty, winey, balsamic, lavender, earthy-mushroom, rosy, vervain and/or sap-like odor.
1.29 Method 1, or any of 1.1-1.28, wherein the compound of Formula 1 is selected from the group consisting of:

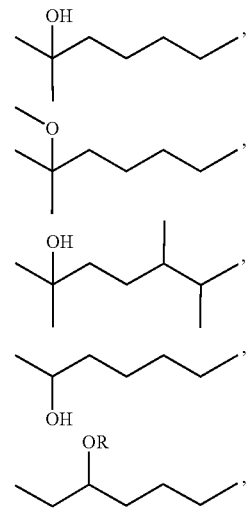

wherein R is H, methyl, formyl or acetyl,

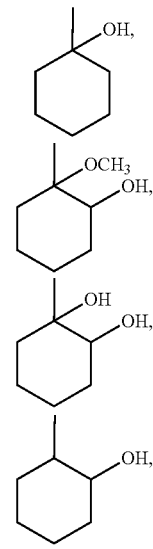

-continued

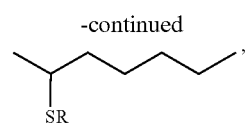

wherein R is H or methyl,

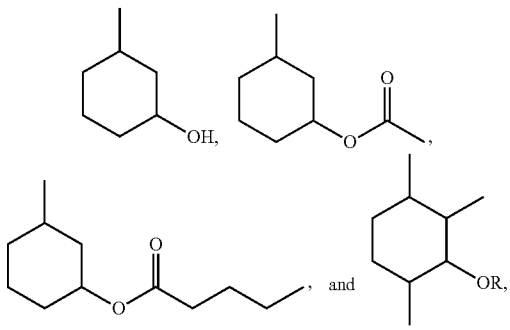

wherein R is H, methyl, ethyl, formyl or acetyl; wherein in each of said compounds any stereogenic center can have any permitted stereochemical arrangement or combinations thereof (e.g., any mixture of enantiomers, diastereomers or pure stereoisomers);

1.30 Method 1, or any of Methods 1.1-1.29, wherein the compound of Formula 2 is selected from citronellol, isocitronellol, dihydromyrcenol, and isopulegol;

1.31 Method 1, or any of Methods 1.1-1.30, wherein step (a) comprises treating the compound of Formula 2 with ozone in a carrier gas (e.g., $O_2$, $N_2$, air, or a mixture thereof) in a suitable solvent (e.g., water, an alcohol, an acid, or a combination thereof) or neat in the compound of Formula 2, optionally at a concentration of 1-15% ozone in the carrier gas, e.g., 2-10% or 3-9%, or 5-7%, such concentration measured w/w or v/v;

1.32 Method 1.31, wherein the suitable solvent for step (a) is selected from water, propanol, isopropanol, n-butanol, s-butanol, t-butanol, acetic acid, propionic acid, butyric acid, formic acid, n-propyl acetate, isopropyl acetate, n-butyl acetate, t-butyl acetate, ethyl propionate, propyl propionate, butyl propionate, methyl butyrate, ethyl butyrate, hexane, cyclohexane, heptane, octane, or a mixture thereof, e.g., wherein the solvent is selected from water, isopropanol, n-butanol, acetic acid, propionic acid, butyric acid, formic acid, n-butyl acetate, cyclohexane, hexane, heptane, or a mixture thereof;

1.33 Method 1.31 or 1.32, wherein step (a) is carried out in a batch reactor;

1.34 Method 1.31 or 1.32, wherein step (a) is carried out in a concurrent flow, falling film reactor;

1.35 Method 1 or any of 1-1.34, wherein the solvent for step (b) comprises water, an alcohol, an acid, or a combination thereof (e.g., selected from water, methanol, ethanol, propanol, isopropanol, butanol, acetic acid, propionic acid, formic acid, or a mixture thereof), or wherein the solvent for step (b) is essentially the neat intermediates from the reaction of step (a), optionally mixed with water;

1.36 Method 1 or any of 1-1.35, wherein the solvent for step (a) is the same as the solvent for step (b);

1.37 Method 1 or any of 1-1.36, wherein the crude product stream from step (a) passes directly into a batch reactor or flow reactor for step (b), e.g., wherein the step (a) product stream is continuously quenched;

1.38 Method 1.37, wherein the continuous quenching comprises adding a solution of the alpha-hydroxysulfinic acid or alpha-hydroxysulfinic acid salt in water to the ozonide product stream from step (a), optionally wherein the aqueous quench solution further comprises a co-solvent or buffer;

1.39 Method 1.38 wherein the cosolvent is a water-miscible organic solvent, such as methanol, ethanol, isopropanol, acetonitrile, DMSO, DMF, dioxane, or tetrahydrofuran;

1.40 Method 1.38 or 1.39, wherein the buffer is an inorganic basic salt such as an alkali metal acetate (e.g., sodium acetate, potassium acetate) or alkali metal phosphate (e.g., sodium phosphate, potassium phosphate), or alkali metal carbonate or bicarbonate (e.g., sodium carbonate, sodium bicarbonate, potassium carbonate, potassium bicarbonate);

1.41 Any one of methods 1.35-1.40, wherein the quenching solution is a solution of hydroxymethylsulfinic acid (or sodium salt thereof) and sodium acetate in water;

1.42 Method 1 or any of 1-1.41, wherein the method does not involve treating any ozonide intermediates with any traditional ozonide quenching reagent (e.g., an acid or base for hydrolysis, a strong oxidizing agent, or a strong reducing agent), for example, wherein the method does not involve any one or more of: dimethyl sulfide, zinc metal, thiourea, triphenylphosphine, a borohydride salt (e.g., sodium borohydride), an aluminum hydride salt (e.g., lithium aluminum hydride), a trialkylborohydride salt, formic acid, hydrogen gas, hydrogen peroxide, a permanganate salt, a chromate salt, a perchlorate salt, a periodate salt, osmium tetroxide, a percarboxylic acid, manganese dioxide, a mineral acid (e.g., HCl, $H_2SO_4$, $HNO_3$, $H_3PO_4$), an organic carboxylic acid, a sulfonic acid, trifluoroacetic acid, trichloroacetic acid, or a hydroxide, alkoxide, carbonate, bicarbonate, or tertiary amine base;

1.43 Method 1 or any of 1.1-1.42, wherein step (b) occurs at a temperature from 0 to 100° C., e.g., between 20 and 80° C., or between 30 and 50° C., or between 5 and 60° C., or wherein step (b) takes place initially at a temperature between 5 and 25° C., and the reaction is subsequently heated to a temperature between 45 and 60° C.

1.44 Method 1 or any of 1.1-1.43, wherein the pH of the step (b) reaction is maintained between 6 to 11, e.g., from 7 to 10, such as by periodic addition of a base or buffer solution.

1.45 Any preceding method, wherein the variables n, X, $R^1$, $R^2$, $R^3$, $R^4$, $R^5$, and $R^6$ are the same as between the compound of Formula 2 as reactant and the compound of Formula 1 as product;

1.46 Any of Methods 1 or 1.1-1.44, wherein the variables n, X, $R^1$, $R^2$, $R^4$, $R^5$, and $R^6$ are the same as between the compound of Formula 2 as reactant and the compound of Formula 1 as product, but wherein the variable $R^3$ is different, e.g., wherein $R^3$ of Formula 2 is H and $R^3$ of Formula 1 is formyl, or wherein $R^3$ of Formula 2 is formyl or acyl and $R^3$ of Formula 1 is H;

1.47 Any preceding method, wherein the method further comprises the step of treating a compound of Formula 1 wherein $R^3$ is H with an acylating agent and suitable base in suitable solvent to form the compound of Formula 1 wherein $R^3$ is $C_{2-10}$acyl;

1.48 Method 1.47, wherein the acylating agent is a compound having the formula $R^3$—O—$R^3$ or $R^3$—Cl (e.g., acetyl chloride, acetic anhydride, propionyl chloride, butyryl chloride, pentanoyl chloride), and the suitable base is selected from a tertiary alkylamine, heterocyclic amine or basic heteroaromatic (e.g., triethylamine, diisopropylethylamine, N-methylmorpholine, N-methylpiperazine, pyridine, pyrimidine, N,N-dimethylaminopyridine, or imidazole);

1.49 Any preceding method, wherein the method further comprises the step of treating a compound of Formula 1 wherein $R^3$ is formyl with a suitable base in suitable solvent to form the compound of Formula 1 wherein $R^3$ is H;

1.50 Method 1.49, wherein the suitable base is an alkoxide base, e.g., a methoxide, ethoxide, propoxide or isopropoxide base (e.g., sodium, potassium, or lithium salt thereof) in an alcoholic solvent (e.g., methanol, ethanol, propanol or isopropanol); or a hydroxide, carbonate, or bicarbonate base (e.g., sodium, potassium, cesium, lithium salt thereof) in water or a water-alcohol mixture;

In a second aspect, the present disclosure provides for use alpha-hydroxysulfinic acid or alpha-hydroxysulfinic acid salt for the quenching of an ozonide mixture, for example, as provided in any of Methods 1 or 1.1-1.50.

In a third aspect, the present disclosure provides a compound of Formula 1 made according to Method 1 or any of 1.1-1.50.

In a fourth aspect, the present disclosure provides a product or composition, such as an organoleptic composition, comprising a compound of Formula 1, made according to Method 1 or any of 1.1-1.50. In some embodiments, the compound of Formula 1 may be used alone as a fragrance or added into a fragrance composition and/or consumer product as an agent for increasing substantivity and/or retention of a fragrance preparation and/or as a fixative.

In a typical reaction according to the present disclosure, the starting material alkene is mixed is cooled to 5° C. (e.g., neat or in a suitable inert solvent) with rapid stirring in a jacketed glass reactor equipped with overhead stirrer and controlled gas diffusion. A mixture of 5-7 wt. % ozone in oxygen or nitrogen carrier gas is then diffused into the mixture at a flow rate of 3 l/min. For example, the ozone may be introduced for 60 minutes or until the alkene starting material is completely consumed, preferably maintaining the temperature at or below 22° C.

In a typical quenching procedure according to the present disclosure, the above mixture is then purged with nitrogen and transferred into a 1 L flask through a pump with the continuous addition of the quenching agent solution, such as an aqueous solution of sodium hydroxymethanesulfinate and sodium acetate, at room temperature over 20 minutes.

The resulting crude mixture may then be slowly warmed up to 50° C., such as over 2 hours, and kept at 50° C. for another 1 hour, or until the peroxide value of the mixture is near zero, such as by standard iodometric titration test. The material may then be treated with sodium chloride solid and stirred for 30 minutes or until all solids are dissolved. Optionally, an organic solvent may then be added, and the organic layer separated, and the purified product obtained by vacuum distillation.

In some embodiments, the reaction product resulting from an initial alcohol starting material comprises an O-formyl ester, optionally mixed with the corresponding alcohol. Without being bound by theory, it is believed that this may result from reaction between the hydroxy group and the hydroxymethyl group of the sulfinic acid reagent. In such instances, alcohol product can be obtained by hydrolyzing these formates compounds with a base including, but not limited to, sodium methoxide, sodium ethoxide, sodium hydroxide and potassium carbonate in methanol.

The two steps of the reaction, ozonolysis and ozonide quenching, may generally be carried out with or without solvent depending on the nature of the starting materials. Suitable solvents for either or both steps include: alcohols, such as methanol, ethanol, propanol, isopropanol, n-butanol, sec-butanol, tert-butanol, and the like; lower carboxylic acid such as formic acid, acetic acid, propionic acid, butyric acid, and the like; ethers, such as diethyl ether, ethyl propyl ether, ethyl butyl ether, dipropyl ether, diisopropyl ether, methyl tert-butyl ether, methyl isopropyl butyl ether, dibutyl ether, and the like; lower alkyl esters of lower carboxylic acids, such ethyl acetate, methyl acetate, n-propyl acetate, isopropyl acetate, n-butyl acetate, t-butyl acetate, ethyl propionate, propyl propionate, butyl propionate, methyl butyrate, ethyl butyrate, and the like; cyclic ethers, such as tetrahydrofuran, dioxane, 1,3-dioxolane, and the like; alkane nitriles, such as acetonitrile, propionitrile, butyronitrile, isobutyronitrile, valeronitrile, and the like; aromatic hydrocarbons, such as benzene, toluene, xylene, anisole, and the like; aliphatic hydrocarbons, such as pentane, hexane, heptane, octane, cyclohexane, cycloheptane, cyclooctane, and the like; water; or any combinations thereof. All these solvents can be used singly or in mixture with each other. Water can also be used as a solvent with or without mixing above mentioned solvents during the reaction.

Preferably, the solvent is a solvent having a flash point above 20° C. and/or a boiling point above 60° C., e.g., a boiling point above 75° C., or above 90° C., or above 110° C.

In some embodiments, the solvent is selected from water, propanol, isopropanol, n-butanol, s-butanol, t-butanol, acetic acid, propionic acid, butyric acid, formic acid, n-propyl acetate, isopropyl acetate, n-butyl acetate, t-butyl acetate, ethyl propionate, propyl propionate, butyl propionate, methyl butyrate, ethyl butyrate, hexane, cyclohexane, heptane, octane, and mixtures thereof. In some embodiments, the solvent is selected from water, isopropanol, n-butanol, acetic acid, propionic acid, butyric acid, formic acid, n-butyl acetate, cyclohexane, hexane, heptane, and mixtures thereof.

The quenching of ozonide product may be achieved by directly adding the quenching agent to the reaction solution from the ozonolysis step. The amount of reducing agent is at least 0.5 equivalent, preferably 0.5 to 1.0 equivalent, based on the molar amount of alkene starting material.

In preferred embodiments, the quenching agent is hydroxymethanesulfinic acid or a salt thereof, such as the sodium salt. Sodium hydroxymethanesulfinate is soluble in aqueous solvents and forms a homogeneous aqueous solution over a wide temperature range (−75° C. to 60° C.).

The quenching step is preferably conducted at a temperature of about 5° C. to 60° C., preferably 22° C. to 50° C. A suitable quenching time is about 15 minutes to 4 hours, preferably 20 minutes to 3 hours.

The pH of the ozonide quenching reaction may be maintained between 6 to 11, preferably 7 to 10. To maintain this range of pH, inorganic base, preferably, sodium acetate, sodium carbonate, sodium bicarbonate, potassium acetate, potassium carbonate and the like is added from time to time.

By way of example, representative reactions within the scope of the present disclosure include, but are not limited to, the following:

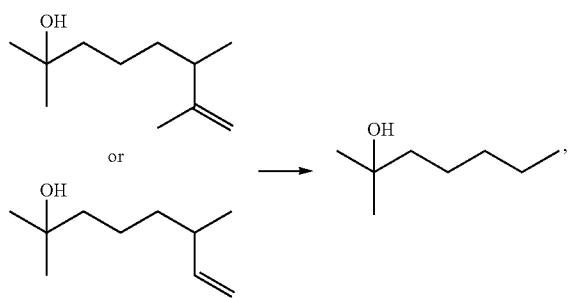

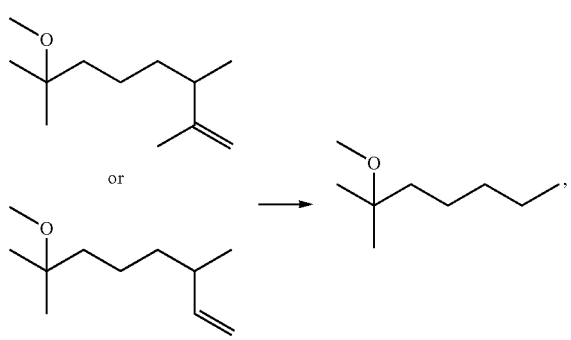

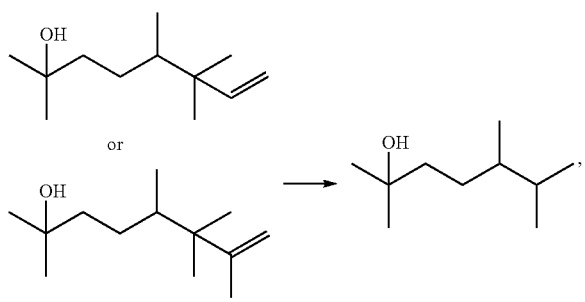

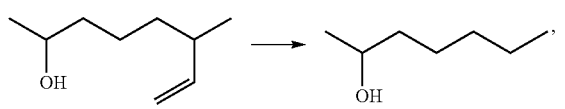

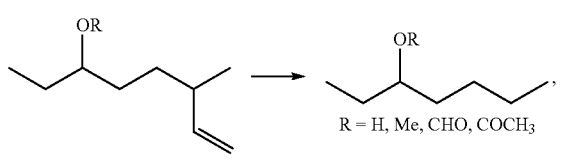

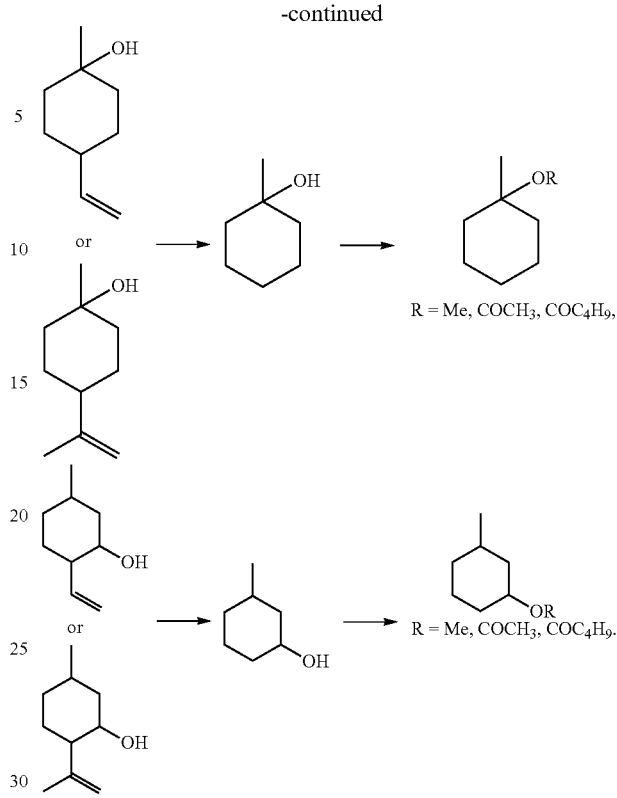

Examples of organoleptic compounds which can be made according to the present disclosure include but are not limited to:

| compounds | smells | Mild/strong |
|---|---|---|
| R-3-Methyl-1-Cyclohexanol | Industrial, plastic | Mild |
| R-2-Methyl-1-Cyclohexanol acetate | Floral, metallic | Mild |
| 2-Methylheptane-2-ol | Pine, Muguet | Strong |

As used herein, the term "alkali metal" includes lithium, sodium, potassium, and rubidium. As used herein, the term "alkaline earth metal" includes beryllium, magnesium, calcium, and strontium. While sodium salts are practical and efficient, lithium, potassium, magnesium, ammonium, and calcium salts can be used as well.

EXAMPLES

Example 1-(R)-3-Methyl-1-Cyclohexanol and Derivatives

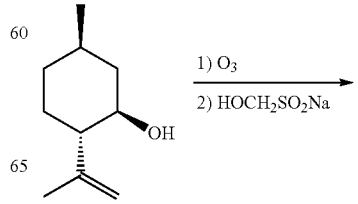

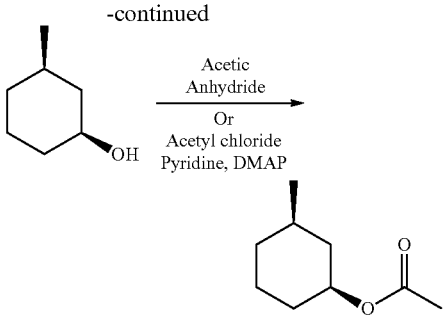

A solution of isopulegol (500 g, 3.2 mol) in 1-butanol (1.5 kg) is pumped through 2 sequential falling film reactors at a flow rate of 1.89 kg/h (Feed 1). The film is contacted with a concurrent-flow gas mixture of 3.7% w/w $O_3/N_2$ gas mixture (Feed 2). The internal reactor temperature is about 19-30° C. Continuous quenching of the product stream is performed using an aqueous solution of hydroxymethanesulfinic acid sodium salt (1000 g, 2 eq.) and sodium acetate (1.5 kg) in water (1.5 kg) at 50-60° C. After quenching is complete, the organic layer is separated and the product, (R)-3-methyl-1-cyclohexanol (106 g; 28% conversion by GC) is obtained by vacuum distillation (pot temperature: 85-90° C.; distillation head temperature: 45-50° C.; pressure: 1.2-2.5 torr).

A mixture of (R)-3-methyl-1-cyclohexanol (6.0 g, 52.6 mmol) and acetic anhydride (9.9 mL, 105.2 mmol) is taken in 50 mL round bottomed flask and heated to 80° C. for 7 hours, until starting material disappeared (monitored by GC). After cooling to ambient temperature, the reaction is quenched with water (5 mL) and stirred for 30 minutes. The solution was diluted with methyl t-butyl ether (40 mL) and water (40 mL). The organic layer is separated and washed with water (40 mL×3), then with saturated sodium bicarbonate solution (40 mL×3). The organic layer is then dried with anhydrous sodium sulfate, filtered, and concentrated in a rotary evaporator. The product, (R)-3-methyl-1-cyclohexanol acetate (7.5 g crude yield; 3.8 g, 46% yield after distillation) is obtained by fractional distillation (pot temperature: 30-40° C.; distillation head temperature: 20-25° C.; pressure: 0.5-0.9 torr).

The same product is also obtained by reacting (R)-3-methyl-1-cyclohexanol (60 g, 526.3 mmol), pyridine (63.8 mL, 789.4 mmol) and DMAP (643 mg, 5.26 mmol) in THF (250 mL) with acetyl chloride (44.9 mL, 631.6 mmol) added dropwise over 20-25 minutes at 0-5° C. The reaction is stirred at that temperature for 3 hours until starting material disappeared, and the product isolated after aqueous work-up and fractional distillation.

Example 2—2-methyl-2-heptanol

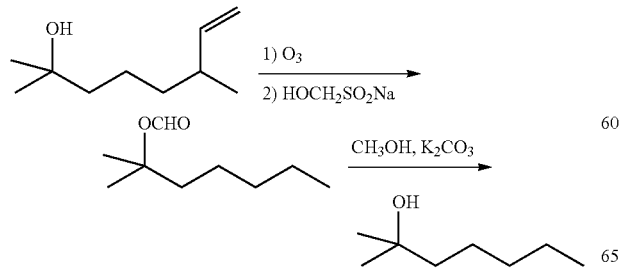

An emulsion of dihydromyrcenol (103 g, 659 mmol) in water (309 g) is taken up in a 500 mL Syrris reactor and stirred vigorously at 5-8° C. Ozone gas (3.7% w/w in $N_2$) is passed through the reaction mixture at a rate of 3 L/minute until the starting material disappeared. The temperature of the reaction is controlled at about 15.6° C. and below. After 3 hours, the reaction is determined to be complete. The reaction mixture is pumped into a 1 L round bottomed flask fitted with a dropping funnel. At a temperature of 45° C., an aqueous solution of hydroxymethanesulfinic acid sodium salt (100.26 g, 659 mmol) and sodium acetate (4 g) in water (150 g) is added over 15 minutes through the dropping funnel. The pH of the solution is maintained around 6-7. Once the addition is completed, the temperature is maintained at 50° C. for another 30 minutes, followed by stirring overnight stirring at ambient temperature. The organic layer is separated, and GC shows 13.0% of 2-methyl-2-heptanol in the mixture and 1.1% 2-methyl-2-heptanol formate. A mixture of 2-methyl-2-heptanol and formate are together isolated by distillation at reduced pressure.

To a solution 2-methyl-2-heptanol and 2-methyl-2-heptanol formate (124 g) in methanol (50 mL) was added potassium carbonate (17 g). The mixture is stirred for 24 hours at ambient temperature. The solution is filtered through a silica gel pad, and the pad is washed with ethyl acetate. The washings and filtrates are combined and concentrated on a rotary evaporator to provide a colorless liquid (116 g). The crude material is further purified by treatment with NaOH/$KMnO_4$ (to wash out olefinic impurities) followed by distillation under reduced pressure (pot temperature: 92° C., pressure: 34-38 torr.) to yield 99% (GC) pure 2-methyl-2-heptanol (68 g, 59% yield).

The Examples provided herein are exemplary only and are not intended to be limiting in any way to the various aspects and embodiments of the invention described herein.

We claim:

1. A method of making a compound according to Formula 1:

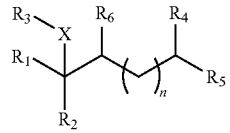

wherein n is an integer from 0-5; X is O or S; $R^3$ is selected from H, $C_{1-6}$alkyl, and $C_{2-10}$acyl; and each of $R^1$, $R^2$, $R^4$, $R^5$, and $R^6$ are independently selected from H and $C_{1-10}$alkyl, optionally wherein each of said $C_{1-10}$alkyl is further substituted by a group selected from $C_{1-6}$alkyl, hydroxy, $C_{1-6}$alkoxy, formyl, and $C_{2-10}$acyl, or wherein $R^1$ and $R^2$, and/or $R^4$ and $R^5$, and/or $R^2$ and $R^5$, can be taken together to form a $C_{3-8}$carbocyclic ring, wherein such ring is optionally substituted by a group selected from $C_{1-6}$alkyl, hydroxy, $C_{1-6}$alkoxy, formyl, and $C_{2-10}$acyl;

wherein the method comprises the steps of (a) treating the compound of Formula 2,

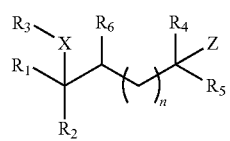

wherein n, X, and each of $R^1$, $R^2$, $R^3$, $R^4$, $R^5$, and $R^6$ are as defined for Formula 1, and wherein Z is selected from vinyl (—CH═CH$_2$) and isopropenyl (—C(CH$_3$)═CH$_2$);

with ozone to form an ozonide mixture, and (b) quenching the ozonide mixture with an alpha-hydroxysulfinic acid or alpha-hydroxysulfinic acid salt quenching agent to yield the compound of Formula 1.

2. The method of claim 1, wherein the quenching agent is an alpha-hydroxysulfinic acid or alpha-hydroxysulfinic acid salt according to the formula:

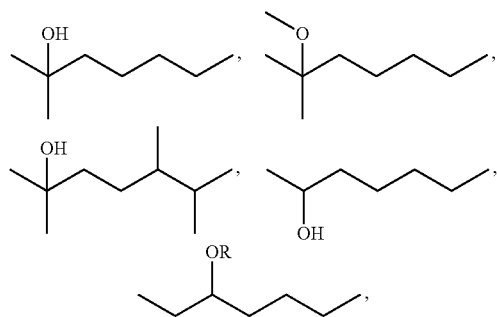

wherein R is H, methyl, formyl or acetyl,

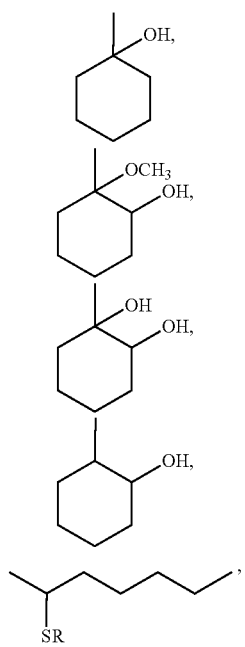

wherein R is H or methyl,

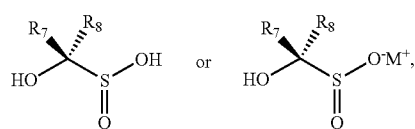

wherein $R^7$ and $R^8$ are each independently selected from $C_{1-6}$alkyl, aryl, and heteroaryl, and wherein M is a metal or ammonium counterion.

3. The method of claim 1, wherein the quenching agent is HOCH$_2$S(O)OH or HOCH$_2$S(O)OM, wherein M is selected from Li, Na and K.

4. The method of claim 1, wherein the quenching agent is HOCH$_2$S(O)ONa.

5. The method of claim 1, wherein X is S.

6. The method of claim 1, wherein X is O.

7. The method of claim 1, wherein $R^3$ is selected from H, methyl, formyl, acetyl, propionyl, butyryl, and pentanoyl.

8. The method of claim 7, wherein $R^3$ is H.

9. The method of claim 1, wherein each of $R^1$, $R^2$, $R^4$, $R^5$, and $R^6$ are independently selected from H and $C_{1-6}$alkyl, optionally wherein each of said $C_{1-6}$alkyl is further substituted by $C_{1-4}$alkyl, hydroxy, $C_{1-3}$alkoxy, formyl, or $C_{2-6}$acyl.

10. The method of claim 1, wherein $R^1$ and $R^2$ and/or $R^4$ and $R^5$ are taken together to form a $C_{3-8}$carbocyclic ring, wherein such ring is optionally substituted by $C_{1-6}$alkyl, hydroxy, $C_{1-6}$alkoxy, formyl, or $C_{2-10}$acyl.

11. The method of claim 1, wherein $R^2$ and $R^5$ are taken together to form a $C_{3-8}$carbocyclic ring, wherein such ring is optionally substituted by $C_{1-6}$alkyl, hydroxy, $C_{1-6}$alkoxy, formyl, or $C_{2-10}$acyl.

12. The method of claim 1, wherein the compound of Formula 1 is selected from the group consisting of:

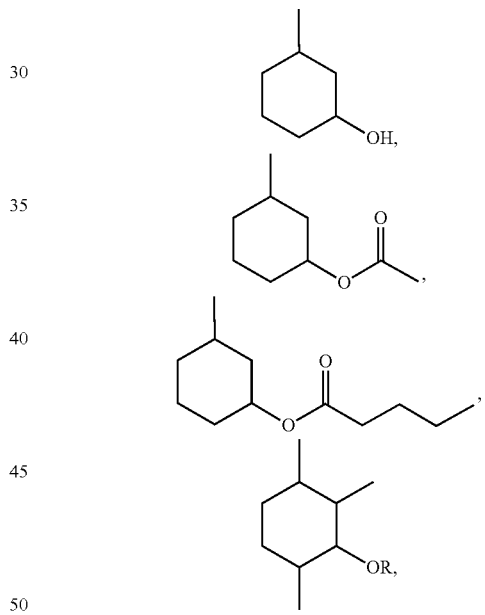

wherein R is H, methyl, ethyl, formyl or acetyl; and wherein in each of said compounds any stereogenic center can have any permitted stereochemical arrangement or combination thereof.

13. The method of claim 1, wherein the compound of Formula 2 is selected from citronellol, isocitronellol, dihydromyrcenol, and isopulegol.

14. The method of claim 1, wherein step (a) comprises treating the compound of Formula 2 with ozone in a carrier gas in a solvent selected from water, propanol, isopropanol, n-butanol, s-butanol, t-butanol, acetic acid, propionic acid, butyric acid, formic acid, n-propyl acetate, isopropyl acetate, n-butyl acetate, t-butyl acetate, ethyl propionate, propyl propionate, butyl propionate, methyl butyrate, ethyl butyrate, hexane, cyclohexane, heptane, octane, and any mixture thereof, or neat in the compound of Formula 2, optionally at a concentration of 1-15% ozone in the carrier gas.

15. The method of claim 14, wherein the solvent for step (a) is selected from water, isopropanol, n-butanol, acetic acid, propionic acid, butyric acid, formic acid, n-propyl acetate, isopropyl acetate, n-butyl acetate, cyclohexane, heptane, octane, and any mixture thereof.

16. The method of claim 1, wherein step (a) provides a crude product stream which passes directly into a batch reactor or flow reactor for step (b).

17. The method of claim 16, wherein the crude product stream provided by step (a) is continuously quenched by adding a solution of the alpha-hydroxysulfinic acid or alpha-hydroxysulfinic acid salt in water to the crude product stream from step (a), optionally wherein the aqueous quench solution further comprises a co-solvent or buffer.

18. The method of claim 17, wherein the buffer is an inorganic basic salt selected from an alkali metal acetate or alkali metal phosphate, or alkali metal carbonate or bicarbonate.

19. The method of claim 1, wherein the method further comprises the step of treating a compound of Formula 1 wherein $R^3$ is H with an acylating agent and a base in a solvent to form the compound of Formula 1 wherein $R^3$ is $C_{2-10}$acyl; or wherein the method further comprises the step of treating a compound of Formula 1 wherein $R^3$ is formyl with a base in a solvent to form the compound of Formula 1 wherein $R^3$ is H.

* * * * *

UNITED STATES PATENT AND TRADEMARK OFFICE
CERTIFICATE OF CORRECTION

Page 1 of 2

PATENT NO. : 11,919,849 B2
APPLICATION NO. : 17/772373
DATED : March 5, 2024
INVENTOR(S) : Patrick Foley et al.

It is certified that error appears in the above-identified patent and that said Letters Patent is hereby corrected as shown below:

In the Specification

Column 9, Line 44, "rate of 3 lmin" should be changed to "rate of 3L/min"

In the Claims

Claim 2, Column 15, Line 11 to 56, delete the chemical structures and text starting after "according to the formula:" and ending with "wherein R is H or methyl,"

Claim 12, Column 16, Line 26, immediately after the phrase "Formula I is selected from the group consisting of:" insert the following chemical structures:

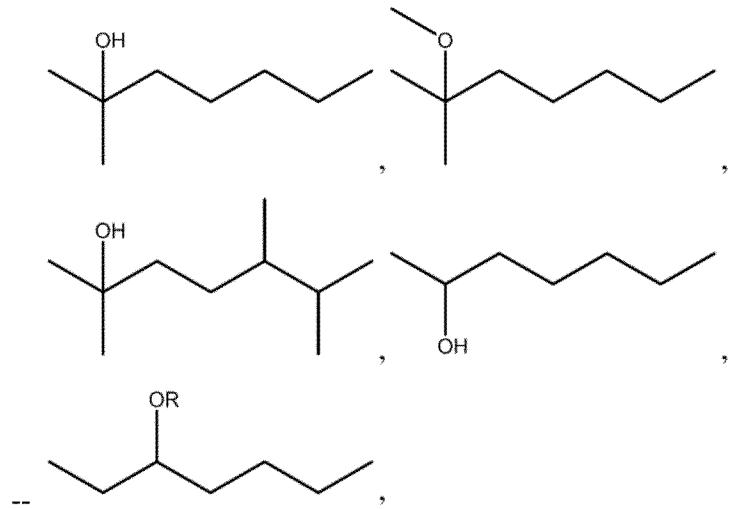

wherein R is H, methyl, formyl or acetyl,

Signed and Sealed this
Twenty-seventh Day of August, 2024

Katherine Kelly Vidal
*Director of the United States Patent and Trademark Office*

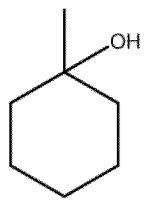
,
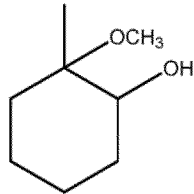
,
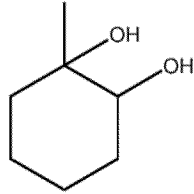
,
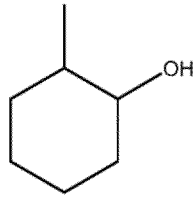
,
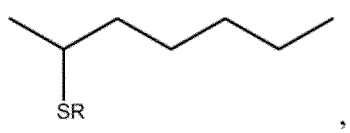
,
wherein R is H or methyl,--